United States Patent [19]

Lynn et al.

[11] Patent Number: 5,019,050
[45] Date of Patent: May 28, 1991

[54] SECURING DEVICE AND METHOD

[76] Inventors: Karen K. Lynn, 10617 E. 26th Terrace, Independence, Mo. 64052; Susan L. Higgins, 5193 SW. Raintree Pkwy., Lee's Summit, Mo. 64082

[21] Appl. No.: 358,415

[22] Filed: May 30, 1989

[51] Int. Cl.⁵ .............................................. A61M 5/32
[52] U.S. Cl. ........................... 604/179; 128/DIG. 15; 128/DIG. 26
[58] Field of Search ...................... 604/179, 180, 174; 128/DIG. 26, DIG. 15

[56] References Cited

U.S. PATENT DOCUMENTS

| | | |
|---|---|---|
| 3,812,851 | 5/1974 | Rodriguez . |
| 3,834,380 | 9/1974 | Boyd . |
| 3,878,849 | 4/1975 | Muller et al. . |
| 3,918,446 | 11/1975 | Buttaravoli . |
| 4,088,136 | 5/1978 | Hasslinger et al. . |
| 4,096,863 | 6/1978 | Kaplan et al. . |
| 4,275,721 | 6/1981 | Olson . |
| 4,316,461 | 2/1982 | Marais et al. . |
| 4,336,806 | 6/1982 | Eldridge, Jr. . |
| 4,445,894 | 5/1984 | Kovacs ........................ 128/DIG. 26 |
| 4,449,527 | 5/1984 | Hinton . |
| 4,470,410 | 9/1984 | Elliott . |
| 4,490,141 | 12/1984 | Lacko et al. . |
| 4,499,975 | 5/1984 | Perry . |
| 4,520,813 | 6/1985 | Young . |
| 4,548,200 | 10/1985 | Wapner ...................... 128/DIG. 26 |
| 4,591,356 | 5/1986 | Christie . |
| 4,662,873 | 5/1987 | Lash et al. . |
| 4,671,787 | 6/1987 | Widman .............................. 604/179 |
| 4,838,867 | 6/1989 | Kalt et al. ........................... 604/180 |

Primary Examiner—Stephen C. Pellegrino
Assistant Examiner—Ralph A. Lewis
Attorney, Agent, or Firm—Litman, McMahon & Brown

[57] ABSTRACT

A securing device comprises a strap having a body with first and second ends, and a fastening system which may comprise a hook-and-loop type fastener. The strap includes first and second fastening strips extending from the body first and second ends. Each fastening strip includes a hook face forming a hook portion of the hook-and-loop fastening system and an adhesive face. The strap body includes an outer material layer forming the loop portion of the fastening system. A method of securing intravenous infusion equipment with the securing device of the present invention is also disclosed.

21 Claims, 3 Drawing Sheets

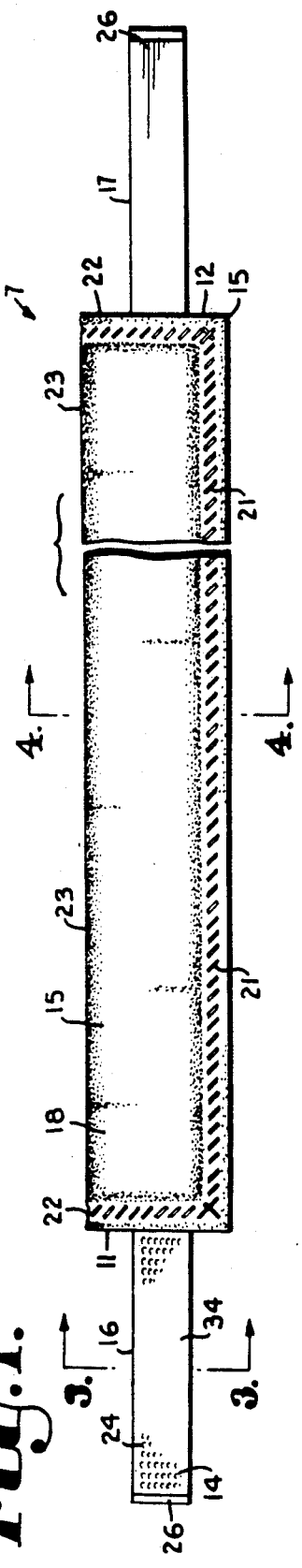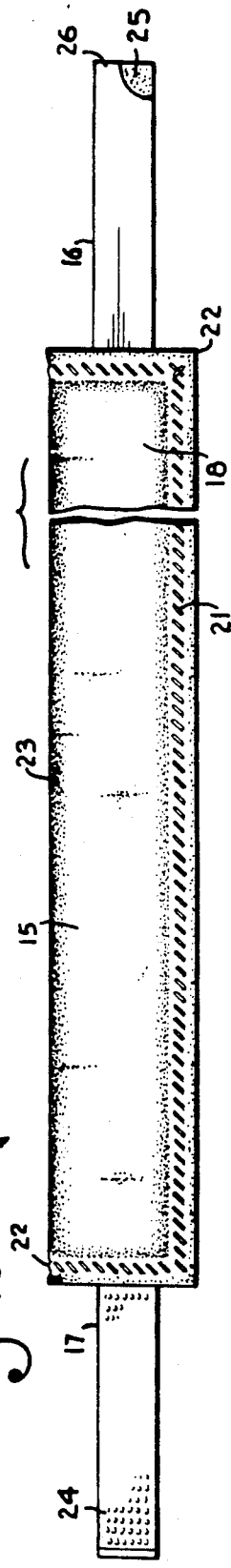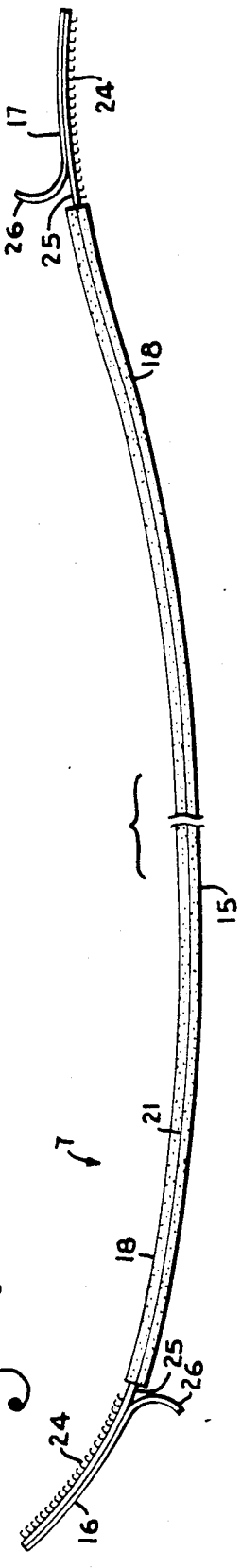

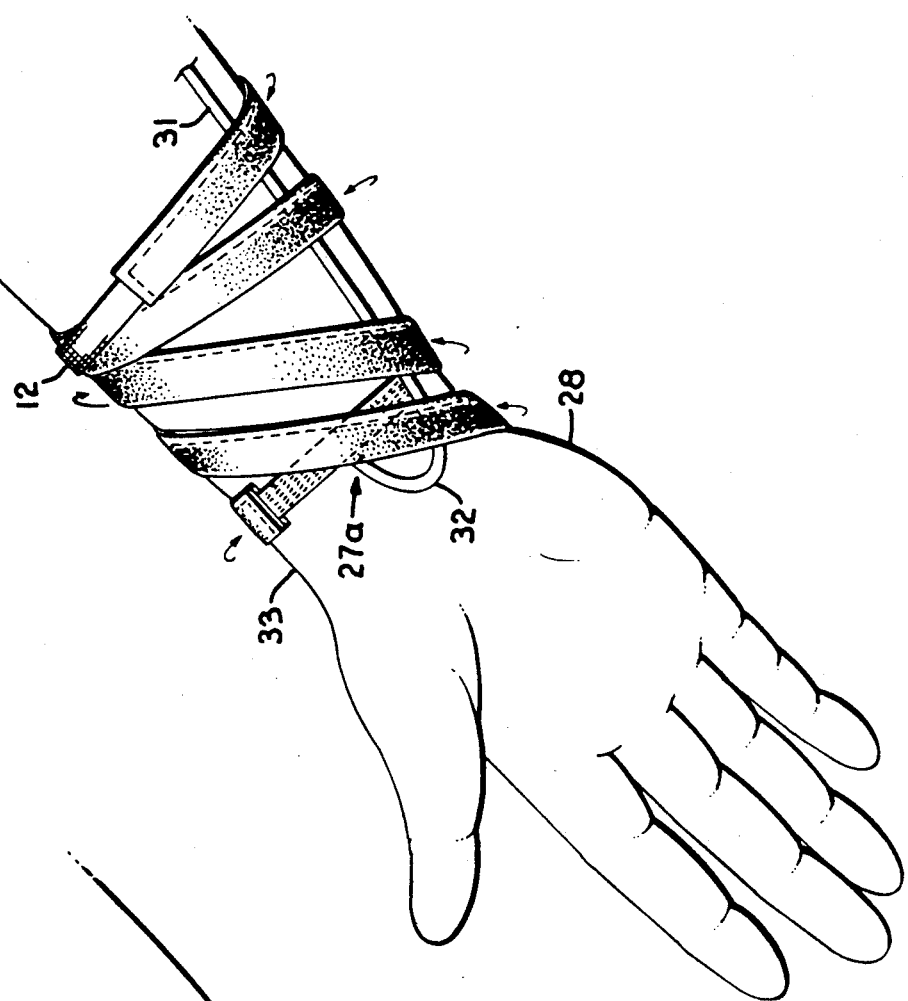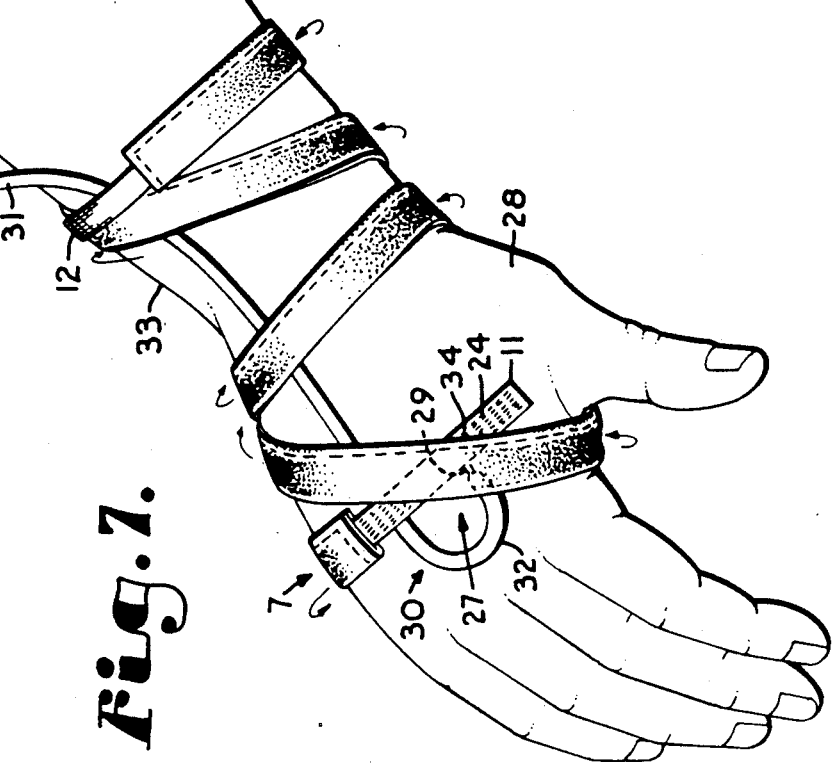

SECURING DEVICE AND METHOD

BACKGROUND OF THE INVENTION

1. Field of the Invention

This invention relates generally to a self-attaching strap and in particular to a device and method for securing an intravenous infusion needle and tubing on a patient during an intravenous infusion and for protecting an intervention site.

2. Description of the Prior Art

In a variety of medical treatment situations, it is often desirable and at times imperative to initiate an intravenous (or "IV") infusion of medications, blood, electrolytes, and similar fluids. It is often of critical importance to accomplish the task of inserting an intravenous needle or catheter into a patient's vein as quickly as possible to expeditiously administer such fluids. For this reason, peripheral veins of the hands, arms, feet and legs are often employed.

A skilled clinician can normally initiate an intravenous infusion rapidly and without assistance, but the insertion site of the intravenous catheter must be secured to prevent accidental removal. This can be an awkward, time-consuming, frustrating procedure for the nurse, physician, or paramedic who initiated the intravenous treatment and must then see to it that the needle or catheter and any excess tubing are secured. In conventional practice, strips of adhesive tape can be applied to the intravenous catheter hub and the excess tubing to secure these respective parts to the patient's skin. If only one member of the medical team has the duty of initiating the intravenous treatment, he or she can tear such strips of tape before starting the procedure, attempt to hold the intravenous equipment in place while tearing the tape, or ask for assistance.

The aforementioned procedure is even more difficult with gloves on, and many health care professionals routinely wear protective gloves when contact with body fluids is likely. Contact with a patient's body fluids is not unlikely when an intravenous treatment is administered. Adhesive tape can stick to the gloves, making application to the patents' skin difficult. The tape can also tear gloves. If gloves are used to insert a needle or a catheter and then removed prior to a taping procedure, very often a powder from the gloves is left on a clinician's hands which interferes with the adhesive properties of the tape.

Conditions of patients' skin such as excessive hair, hypothermia, increased fragility and the like can interfere with tape adhesion. Furthermore, excessive hair and fragile skin can make removal of tape painful to patients.

In response to such conditions of their patients' skin, it has been a practice of some health care professionals to avoid tape by using strips of gauze for wrapping patients' limbs and thus securing intravenous equipment. This procedure can also be cumbersome to employ and can interfere with inspection of insertion sites for dislodgment or infiltration difficulties.

There are known in the prior art several devices for securing intravenous catheters and tubing to patients. While some prior art securing devices were proposed to alleviate certain of the aforementioned problems, for one reason or another they have generally proven to be unsatisfactory.

In general, these prior art devices appear complicated to use and uncomfortable to the patient. Many involve combinations of fasteners, tube mounting members, bands, or large adhesive areas which could cause application delays, and removing them could be painful or at least difficult. The complicated constructions of some prior art devices tend to make them difficult to manufacture and therefore unduly expensive.

The appearances of some prior art devices are so unsightly and aesthetically undesirable that they may produce emotional distress in sensitive patients. The complicated and sometimes fragmented designs of some prior art devices could render them unrealistic in actual practice, especially in emergency situations, and perhaps explains why tape and dressing techniques are still commonly employed methods for securing intravenous needles or catheters and tubing.

SUMMARY OF THE INVENTION

In the practice of the present invention, a securing device is provided which comprises a strap with a body having first and second ends. A hook-and-loop fastening system is provided and includes first and second fastening strips mounted on the body first and second ends respectively. Each fastening strip includes an adhesive face adapted for adhesive, releaseable attachment to a patient's skin and a hook face forming a hook portion of the hook-and-loop fastening system. The strap body includes an outer material layer forming the loop portion of the hook-and-loop fastening system. The present invention also includes a method of fastening intravenous infusion equipment with the securing device of the present invention.

OBJECTS OF THE INVENTION

It is therefore a primary object of the invention to provide rapidly applied means for securing an intravenous needle or catheter hub at the site of insertion in a patient's vein and for protecting the catheter from accidental dislodgment or removal; to provide means for supporting intravenous tubing connected to an intravenous catheter; to provide means to retain intravenous tubing close to patients' limbs, thereby protecting intravenous sites against sudden jerks on the tubing; to provide a relatively simple device for securing intravenous catheters and tubing in an uncomplicated, expedient fashion, thereby preventing unnecessary delays in administering life-saving treatments; to provide a securing device and method of applying same which can be easily accomplished while wearing protective gloves to minimize potential exposure to infectious blood-carrying diseases from venipunctures; to provide a securing device comprising a self-attaching strip and method of applying same which are simple in design and concept thereby facilitating their application in emergency situations by clinicians; to provide a securing device which is simple in construction and material which makes it inexpensive to manufacture and therefore cost effective; to provide a device for practically universal adult and pediatric application which may be applied to most peripheral intravenous sites and which adapts automatically to variations in the limb sizes of most intravenous treatment patients; to provide a securing device which can be sterilized and packaged to maintain the sterile integrity of such, and which can be applied aseptically to reduce the risk of nasocomial infection at an intervention site; to provide a securing device and method of applying same which incorporates soft, absorbant, lightweight material, and which operates with minimal adhesives to provide optimal benefits in its application to patients whose skin surfaces are diaphoretic, soiled, hairy, cold, tape sensitive, fragile, or otherwise impaired, and which decreases patient discomfort during its removal; to provide a securing device and method of applying same which can operate independently of or in conjunction with tape, dressings, arm boards and informative labels to increase the security of intravenous injection sites and which can be used to retain various treatment devices in their proper positions on the patients' limbs; and to provide a securing device which is aesthetically acceptable to the patient and which allows for more normal use of the limbs to which the intervention means is applied which can reduce emotional distress in sensitive patients.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary, top plan view of a securing device embodying the present invention.

FIG. 2 is a fragmentary, bottom plan view of the securing device.

FIG. 5 is a side elevational view of the securing device.

FIG. 7 is a perspective view of the securing device, shown being applied to a patient according to the method of the present invention.

FIG. 8 is a perspective view of the securing device, shown applied to a patient according to the method of the present invention in an alternative location.

DETAILED DESCRIPTION OF THE PREFERRED EMBODIMENT

I. Introduction and Environment

Figure 3:
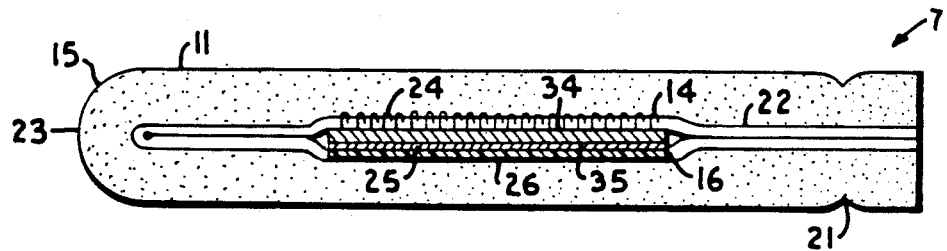
FIG. 3 is an enlarged, transverse, cross-sectional view of the securing device taken generally along line 3—3 in FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 7 generally designates a securing device or selfattaching strap embodying the present invention. The strap 7 generally comprises a longitudinally-extending body 15 with first and second fastening strips 16, 17 attached to and extending from opposite ends thereof.

The device 7 is disclosed in connection with a method for fastening intervention equipment, e.g. an intravenous catheter or needle and a fluid tube, on a patient, which method is practiced according to the method of the present invention.

II. Strap Body 7

A hook-and-loop fastening system 14 is provided for connecting either or both of the fastening strips 16 and 17 to the body 15. The strap body 15 preferably comprises a material with appropriate characteristics to form the loop portion of the hook-and-loop fastening system 14. The materials for constructing a suitable fastening system 14 are available from the Velcro Corporation under its trademark VELCRO. However, various other fastening systems may be employed with the fastening device of the present invention, including other hook-and-loop type fastening systems.

The body 15 preferably includes an outer layer 18 of a suitable loop-type material, e.g. polyester or nylon. An inner material layer 19 comprising, for example, foam rubber or the like can be placed behind or inside of the outer layer 18. A backing material layer 20 can be attached to the outer and intermediate material layers 18, 19 whereby the intermediate material layer 19 is sandwiched between the outer and backing material layers 18, 20. The backing material layer 20 can comprise, for example, canvas.

Figure 4:
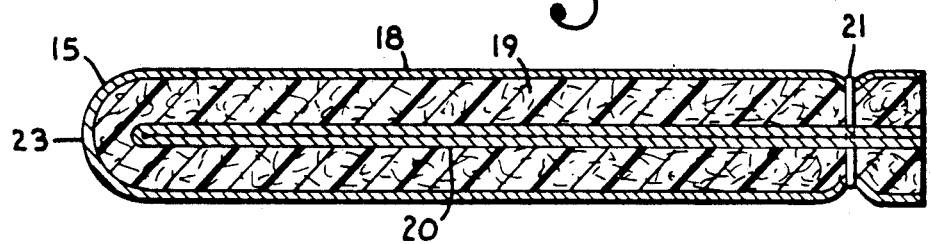
FIG. 4 is an enlarged, transverse, cross-sectional view of the securing device taken generally along line 4—4 in FIG. 1.
Figure 6:
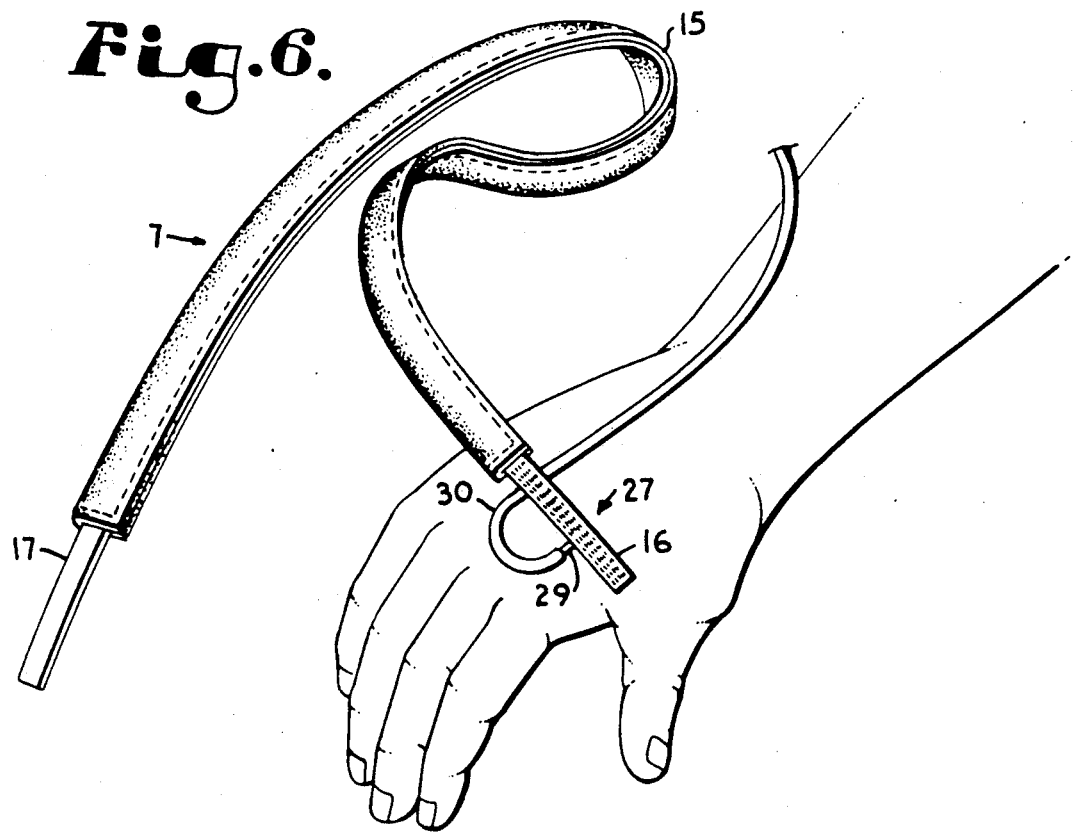
FIG. 6 is a perspective view of the securing device, shown being applied to a patient according to the method of the present invention.

As shown in FIG. 4, the body 15 may be folded longitudinally on itself whereby the backing material layer 20 is doubled over in opposing relation on the inside of the body 15 and the outer material layer 18 presents opposite, outside faces of the body 15. The body 15 may be secured in this folded configuration by a longitudinal seam 21 extending longitudinally along one edge of the body 15 and by a pair of end seams 22 located at opposite first and second body ends 11, 12. The seams 21, 22 can be formed by sewing with any appropriate stitch.

The outer, intermediate and backing layer materials 18, 19 and 20 are preferably chosen for their suitable characteristics in connection with the function of the strap 7. In addition to its loop function in the fastening system 14, the outer material layer 18 should be suitable for direct contact with the skin of a patient. Thus, the outer material layer 18 should not be abrasive and should not be likely to produce allergic reactions in a significant number of patients.

The intermediate material layer 19 should be resilient, such as foam rubber so that it will provide padding for the patient and also tend to conform to the intervention equipment for retaining it in place. The backing material layer 20 is preferably chosen to provide structural integrity for the body 15, and can be chosen for tensile strength whereby the body 15 will remain relatively stable dimensionally, even if pulled upon. In its folded configuration, the body 15 forms a longitudinally-extending folded edge 23 positioned opposite to and extending parallel with the longitudinal seam 21.

The body 15 thus preferably combines the advantages of patient comfort, compatibility with hook-type fasteners, resiliency, tensile strength and dimensional stability. Without limitation on the generality of useful dimensions of the body 15, for attaching intervention equipment to the limbs of patients twenty-seven inches has been found to be a generally suitable length.

III. Fastening Strips 16 and 17

The first and second fastening strips 16 and 17 can be substantially identical, and are preferably attached at the end seams 22 to the first and second body ends 11, 12. The fastening strips 16, 17 extend from the respective body ends 11, 12 in longitudinal alignment with the body 15.

Each fastening strip 16, 17 comprises fastening means for a respective body end 11, 12, and preferably each fastening strip 16, 17 includes two independent fastening means on opposite faces thereof: a male or hook-type material 24 comprising the hook portion of the hook-and-loop fastening system 14; and an adhesive material 25. The adhesive material 25 is covered with a suitable removable backing or cover material 26 until ready for use. As shown in FIG. 5, the fastening strips 16, 17 are oppositely oriented whereby each side of the strap 7 includes both an adhesive material fastening strip face 25 and a hook material fastening strip face 24.

The adhesive material 25 may comprise any of a variety of suitable adhesives for releaseable adherence to patients' skin. Without limitation on the generality of useful dimensions of the fastening strips 16, 17, they can have lengths of approximately four and one-half inches and widths of approximately one-half inch.

IV. Fastening Method

According to the fastening method of the present invention, the strap 7 can be coiled or folded in any suitable manner which facilitates packaging, sterility, storage and convenient access for quick application.

Interference from the hook material can be avoided by doubling such fastening strip hook material faces 24 on themselves whereby the hook material 24 is prevented from adhering to any other parts of the strap 7. Alternatively, the hook material 24 can be used to secure the strap 7 in a coiled or folded configuration. The hook-and-loop fastening system 14 generally functions by engaging when the hook material 24 is pressed against the body outer material layer 18, and by releasing when said materials are peeled apart. Thus, the hook-and-loop fastening system 14 can be attached, released and reattached an indefinite number of times for adjusting the strap 7 or for reusing it.

Because the fastening strips 16, 17 are substantially identical except for their opposite orientations, either end can be applied first. This symetrical, apply-either-end-first feature of the strap 7 contributes significantly to its convenience of operation, and in fact can be quite important in medical emergencies and similar situations where speed and accuracy may be important factors in the success or failure of medical treatment. For example, fluids are often administered intravenously to emergency and trauma patients for purposes such as stabilizing them, replacing lost blood, etc. Medical practitioners often initiate such treatments at accident sites, in emergency vehicles such as ambulance and helicoptors, and in hospital emergency rooms. In fact, in some emergency medical situations a medical practitioner may be administering intravenous treatment to a patient who is being wheeled about on a hospital gurney or similar device. Under such circumstances automatic, reflexive action by health care practitioners can be critical. It will be appreciated that the symetrical feature of the strap 7 embodying the present invention facilitates such prompt medical treatment because the health care practitioner can quickly and positively apply either fastening strip 16 or 17 without having to consider which should go first. Although the securing method of the present invention is described herein in connection with intervention equipment 30, it will be appreciated that the securing device and method could be utilized to secure various other devices in a wide variety of environments.

The intervention equipment 30 includes a catheter or needle 29 fluidically connected to a tube 30, which in turn is connected to a fluid source (not shown). FIG. 7 shows the catheter 29 inserted at an intervention site 27 on the back of a patient's hand 28. The intravenous tube 31 doubles back to extend along the patient's arm and is secured thereto by the strap 7. The strap 7 is applied by removing the adhesive backing or cover material 26 from either fastening strip 16 or 17, which strip is then adhesively secured to the intervention site 27 by pressing on the hook material face 24.

It will be appreciated that the strap 7 can be packaged in a sterile manner for direct application of the adhesive material 25 to the intervention site 27; alternatively, a sterile wound dressing (not shown) may be applied to the intervention site 27, for application of the adhesive material 25 to the wound dressing. By providing a transparent dressing, the intervention site 27 can be observed for possible fluid infiltration into the surrounding tissue and for dislodgment of the catheter or needle 29.

As shown in FIG. 7, the adhesive material 25 can secure both the catheter 29 and a section of the tube 31 upstream of its U-bend 32. The strap body 15 can then be wound around the patient's hand, wrist and forearm as shown. On one or more of these passes, the body 15 can overlie a portion of the hook material 24, whereby light pressure therebetween can engage the hook-and-loop fastening system 14.

The second fastening strip 17 can be used to secure the strap 7 at a location on the patient's body in spaced relation from the intervention site 27. The adhesive material 25 of the second fastening strip 17 need not be exposed for this step, since the hook material 24 can be used for releaseable fastening directly to the strap body 15. According to the method of the present invention described above, the strap 7 adhesively fastens to the patient only in the area of the intervention site 27, although both ends of the strap 7 can be securely fastened at spaced locations. However, in a variation on the method of the present invention, the second fastening strip 17 can be adhesively fastened to the patient's body by folding the second fastening strip 17 under the body 15 to engage the hook-and-loop fastening system. The adhesive backing or cover material 26 can then be removed, whereby the adhesive material 25 can be pressed against the patient's skin to secure the body second end 12.

FIG. 8 shows an alternative wrapping sequence for the strap 7 of the present invention to secure a catheter 29 at an intervention site 27a located on a patient's wrist 33. As shown, the hook material 24 of the first fastening strip 16 engages the strap body 15 in two places, i.e. on two turns or passes of the strap body 15.

It will be appreciated that the securing device or self-attaching strap 7 according to the present invention can be utilized on various parts of patients' bodies and for attaching various types of medical equipment in various configurations. The ease and speed with which the securing method of the present invention can be practiced will also be appreciated. For example, the cooperation between the two fastening means (i.e. adhesive and hook-and-loop) of both ends of the strap should facilitate its application. If necessary, a health care practitioner could possibly apply the strap 7 utilizing only one hand, leaving the other hand free for maintaining balance in a moving vehicle, for holding an intravenous bottle, for administering other medication or for restraining a patient. It is anticipated that the securing method of the present invention can be performed in a time period as short as ten seconds or less, as compared to conventional taping techniques which could take 10 minutes.

The step wherein the first fastening strip 16 is adhesively attached is useful for starting the securing method, but may not be particularly critical. For example, a patient's skin condition may be such (e.g. oily, wet, dirty, etc.) that the adhesive material 25 will not adhere very well. In this situation the health care practitioner simply utilizes the hook-and-loop fastening system 14 to secure the first loop of the strap 7 in place. Remaining loops of the strap 7 can be placed where needed to further secure the attachment.

The composition of the strap body 15 facilitates the operation of the strap 7. The outer material layer 18 provides the loop portion of the fastening system 14 and is preferably comfortable to the patient. The resilient intermediate layer 19 retains the tube 31 in position without pinching or collapsing it. The backing material layer 20 provides tensile strength and dimensional stability so that the strap 7 will not stretch unduly.

As a further alternative to the intervention site attachments shown in FIGS. 7 and 8, some health care practitioners prefer a "chevron" procedure for fastening catheters, needles, etc. whereby adhesive tape strips form V-shaped patterns for securing the intravenous catheter or tubing in place. The fastening strips 16, 17 of the strap 7 can also be employed in chevron configurations by wrapping them around the intravenous tube 31 with respective end portions of the strips 16 or 17 forming V-shaped or chevron configurations when adhesively secured to the patient.

Although there are advantages to providing similar fastening strips 16 and 17 on both body ends 11, 12 as described above, it will be appreciated that the present invention could be practiced with a fastening strip at only one end of the body, or each end could be provided with only one fastening means, e.g. adhesive material 25 on the first fastening strip 16 and hook material 24 on the second fastening strip 17, or vice versa. Furthermore, the body 15 could comprise a single layer of a suitable material.

An advantage of the securing device and method of the present invention is that, unlike previous gauze and tape securing devices and methods, errors in application can be easily and quickly rectified. Likewise, due to the ease of operation of the securing device, repositioning and adjustments can be easily and quickly accomplished.

It is to be understood that while certain forms of the present invention have been illustrated and described herein, it is not to be limited to the specific forms or arrangement of parts described and shown.

What is claimed and desired to be secured by Letters Patent is as follows:

1. A securing device which includes:
   (a) a strap body with first and second edges, an outer material layer, an intermediate, resilient material layer, and a backing material layer;
   (b) first fastening means associated with one of said ends and including adhesive fastening means;
   (c) second fastening means associated with the other of said ends and including mechanical fastening means;
   (d) said body being folded longitudinally on itself with said backing material layer positioned in opposed relation to itself and substantially surrounded by said intermediate material layer; and
   (e) said outer material layer substantially surrounding said intermediate material layer; and
   (f) means for maintaining said body in its folded position.

2. The device according to claim 1 wherein:
   (a) said first fastening means comprises a fastening strip extending from one of said body ends and including an adhesive material.

3. The device according to claim 1 wherein: (a) said second fastening means includes a hook-and-loop fastening system.

4. The device according to claim 3 wherein said hook-and-loop fastening system includes:
   (a) said body comprising a loop material; and
   (b) said second fastening means comprising a strip extending from said body second end and including a hook material adapted for releaseable engagement with said body.

5. The device according to claim 1 wherein each said fastening means comprises:
   (a) a fastening strip extending from a respective body end and including an adhesive face with an adhesive material thereon and a hook face with a hook material thereon, said adhesive face comprising part of said adhesive and said hook material comprising part of said mechanical fastening means; and
   (b) said body including a loop material adapted for releaseable engagement with said hook material.

6. The device according to claim 5 wherein said body includes:
   (a) a first face on the side of said first fastening strip adhesive face and said second fastening strip hook face; and
   (b) a second face on the side of said first fastening strip hook face and said second fastening strip adhesive face.

7. The device according to claim 1 wherein:
   (a) said adhesive fastening means includes a removeable cover over said adhesive material.

8. The device according to claim 1 wherein said body includes:
   (a) an outer material layer;
   (b) an intermediate, resilient material layer; and
   (c) a backing material layer.

9. The device according to claim 1 wherein said body includes:
   (a) a folded edge extending longitudinally therealong;
   (b) a longitudinal seam opposite said folded edge whereat said body is secured together in folded relationship; and
   (c) end seams at said body ends.

10. In combination with intervention equipment comprising a catheter or a needle adapted for intravenous insertion at an intervention site and an intravenous tube communicating therewith, the improvement of a securing device, which comprises:
    (a) an elongated strap body with first and second ends;

(b) first and second fastening strips each attached to and extending longitudinally from a respective body end and including:
  (1) an adhesive face with adhesive material adapted for releaseable attachment to the intervention site; and
  (2) a hook face including a hook fastener material;
(c) said body including a loop material adapted for releaseable attachment to said hook material.

11. The securing device according to claim 10 wherein said body includes:
  (a) a first face on the side of said first fastening strip adhesive face and said second fastening strip hook face; and
  (b) a second face on the side of said first fastening strip hook face and said second fastening strip adhesive face.

12. The securing device according to claim 10 wherein each said fastening strip includes:
  (a) a removable cover adapted for covering said adhesive face.

13. The device according to claim 10 wherein said body includes:
  (a) an outer material layer;
  (b) an intermediate, resilient material layer; and
  (c) a backing material layer.

14. The securing device according to claim 13 wherein:
  (a) said body is folded longitudinally on itself with said backing material layer positioned in opposed relation to itself and substantially surrounded by said intermediate material layer; and
  (b) said outer material layer substantially surrounds said intermediate material layer.

15. The securing device according to claim 14 wherein said body includes:
  (a) a folded edge extending longitudinally therealong;
  (b) a longitudinal seam opposite said folded edge whereat said body is secured together in folded relationship; and
  (c) end seams at said body ends.

16. A method of securing intravenous equipment including a needle or catheter adapted for intravenous placement at an intervention site and an intravenous tube fluidically communicating therewith, which comprises the steps of:
  (a) placing a strap first end at the intervention site;
  (b) winding the strap around a portion of the patient's body;
  (c) mechanically fastening said strap first end to a portion of said strap longitudinally spaced from its first end; and
  (d) releaseably fastening a second end of said strap to one of the strap and the patient.

17. The method according to claim 16, which includes the additional step of:
  (a) mechanically fastening said strap first end to said strap body with a hook-and-loop fastening system.

18. The method according to claim 16, which includes the additional step of:
  (a) mechanically fastening said strap second end to said strap body with a hook-and-loop fastening system.

19. The method according to claim 16, which includes the steps of:
  (a) providing both of said strap ends with fastening strips each including a hook face with a hook material and an adhesive face with an adhesive material; and
  (b) providing said strap body with a loop material adapted for releaseable engagement with said hook material.

20. A securing device which includes:
  (a) an elongated strap body with first and second ends;
  (b) a first fastening strip attached to and extending longitudinally from said first body end and including:
    (1) an adhesive face with adhesive material;
    (2) a hook face including a hook fastener material; and
    (3) said first fastening strip including opposite faces with said adhesive face being located on one of said opposite faces and said hook face being located on the other of said opposite faces;
  (c) a second fastening strip attached to and extending longitudinally from the second body end and including a hook face with a hook fastener material; and
  (d) said body including a loop material adapted for releasable attachment to said hook material.

21. The device according to claim 20 wherein:
  (a) said body is folded longitudinally on itself with said backing material layer positioned in opposed relation to itself and substantially surrounded by said intermediate material layer; and
  (b) said outer material layer substantially surrounds said intermediate material layer.

* * * * *